(12) United States Patent
Djoharian et al.

(10) Patent No.: US 12,254,731 B2
(45) Date of Patent: Mar. 18, 2025

(54) PORTABLE AND SINGLE-USE DEVICE FOR ACCESSING AN AREA WITH RESTRICTED ACCESS, ASSOCIATED ACCESS KEY GENERATION SYSTEM AND ASSOCIATED ACCESS CONTROL METHOD

(71) Applicant: GRAPHEAL, Grenoble (FR)

(72) Inventors: Behnaz Djoharian, Biviers (FR); Vincent Bouchiat, Biviers (FR)

(73) Assignee: GRAPHEAL, Grenoble (FR)

( * ) Notice: Subject to any disclaimer, the term of this patent is extended or adjusted under 35 U.S.C. 154(b) by 246 days.

(21) Appl. No.: 17/997,938

(22) PCT Filed: May 6, 2021

(86) PCT No.: PCT/FR2021/050778
§ 371 (c)(1),
(2) Date: Nov. 4, 2022

(87) PCT Pub. No.: WO2021/224578
PCT Pub. Date: Nov. 11, 2021

(65) Prior Publication Data
US 2023/0177905 A1    Jun. 8, 2023

(30) Foreign Application Priority Data

May 7, 2020    (FR) ...................................... 2004576

(51) Int. Cl.
*G07C 9/26*    (2020.01)
*G07C 9/29*    (2020.01)
*G16H 40/63*    (2018.01)

(52) U.S. Cl.
CPC .................. *G07C 9/26* (2020.01); *G07C 9/29* (2020.01); *G16H 40/63* (2018.01)

(58) Field of Classification Search
CPC . G07C 9/26; G07C 9/29; G16H 10/60; A61B 5/165; A61B 5/681; G01N 27/3272
See application file for complete search history.

(56) References Cited

U.S. PATENT DOCUMENTS

| 4,621,643 A | 11/1986 | New, Jr. et al. |
| 5,209,230 A | 5/1993 | Swedlow et al. |

(Continued)

OTHER PUBLICATIONS

Bandodkar et al., "Battery-free, skin-interfaced microfluidic/electronic systems for simultaneous electrochemical, colorimetric, and volumetric analysis of sweat", Science Advances, vol. 5, No. 1, Jan. 18, 2019, p. eaav3294, 1-15.

(Continued)

*Primary Examiner* — Vernal U Brown
(74) *Attorney, Agent, or Firm* — ArentFox Schiff LLP

(57) ABSTRACT

The disclosure relates to a device for accessing an area with restricted access or an area to which access is controlled, comprising a support, a sensor and access control stage, the support comprising a portion to be discarded and a portion to be retained, the sensor being borne by the portion to be discarded and being configured to measure at least one parameter of a subject's health, and to deliver a detection signal representative of the measurement of each health parameter, the access control stage being borne by the portion to be retained and being configured to store access information dependent on the detection signal delivered by the sensor, the portion to be retained being able to be mechanically separated from the portion to be discarded so as to form an access key allowing, depending on the access information, access or otherwise to the area with restricted access or to the area to which access is controlled.

19 Claims, 1 Drawing Sheet

(56) References Cited

U.S. PATENT DOCUMENTS

| | | | |
|---|---|---|---|
| 11,471,078 B1* | 10/2022 | Davis | G01J 3/28 |
| 2003/0225324 A1 | 12/2003 | Anderson et al. | |
| 2008/0295152 A1 | 11/2008 | Goi | |
| 2017/0206329 A1* | 7/2017 | Capocasale | G16H 10/60 |
| 2018/0220947 A1* | 8/2018 | Bedell, Jr. | A61B 5/02416 |
| 2019/0262827 A1* | 8/2019 | Lalonde | G01N 21/77 |

OTHER PUBLICATIONS

Kim et al., "Wearable biosensors for healthcare monitoring", Feb. 25, 2019, vol. 37, No. 4, p. 389-406.
International Search Report and Written Opinion mailed, Sep. 9, 2021, for PCT/FR2021/050778.

* cited by examiner

PORTABLE AND SINGLE-USE DEVICE FOR ACCESSING AN AREA WITH RESTRICTED ACCESS, ASSOCIATED ACCESS KEY GENERATION SYSTEM AND ASSOCIATED ACCESS CONTROL METHOD

CROSS-REFERENCE TO RELATED APPLICATIONS

This application is a National Phase of PCT/FR2021/050778, filed on May 6, 2021, which claims priority to FR Application No. FR2004576, filed on May 7, 2020, the disclosures of which are hereby incorporated by reference in their entireties.

TECHNICAL FIELD

The present invention relates to a portable and single-use device for accessing a restricted-access area. The invention also relates to an access key generation system comprising such an access device, and a method for controlling access to a restricted-access area.

The invention applies to the measurement of health parameters in humans or animals, especially the analysis of biological samples, in particular the analysis of biological samples obtained from persons or animals susceptible of carrying a pathogenic agent, with a view to authorizing or not authorizing their access to a restricted-access area where it is sought to limit the risk of contamination.

PRIOR ART

It is known to seek to determine whether the health conditions of a subject, that is to say of a living being such as a person or an animal, are compatible with their admission to a restricted-access area. Such an evaluation is meaningful, for example, in the control of infectious epidemics which are likely to lead to real health-related, humanitarian and economic catastrophes, sometimes on a global scale, and of which the damaging effects are likely to register for the long term. The COVID-19 epidemic is a perfect example of this.

Current solutions generally consist in testing a biological sample taken from the subject for whom it is desired to determine whether or not they are allowed to access the restricted-access area. Alternatively or jointly, such a test is carried out directly on the subject.

The term "restricted access" is understood to mean an area to which access is strictly reserved for a certain category of persons or animals, or an area for which it is desirable to control the admission flow.

The term "health parameter" is understood, within the context of the present invention, to mean a biological, physiological or chemical parameter making it possible to qualify and/or quantify a condition associated with the health of a person or an animal.

The term "biological sample" is understood, within the context of the present invention, to mean a liquid, gaseous or solid sample which is taken from a subject, and for which it is desired to determine whether it comprises at least one predetermined analyte. The biological sample may come from any biological source, such as a physiological fluid, including blood, saliva, eye fluid, cerebrospinal fluid, sweat, urine, stools, semen, milk, ascitic fluid, mucous membranes, synovial fluid, peritoneal fluid, amniotic fluid, tissues, cultured cells or the like.

A collected biological material is able to be used as a biological sample directly in the form in which it is obtained when it is taken, or at the end of a pretreatment carried out to modify its character. For example, an initially solid or semi-solid biological material can be made liquid by dissolving or suspending it in a suitable liquid medium.

The term "analyte" is understood, within the context of the present invention, to mean a compound of biological origin which may be a nucleic acid or a protein derived in particular from a contaminating microorganism, possibly an infectious one, for which it is sought to determine the presence in the biological sample and/or the concentration. In particular, the present invention may be very useful for detecting a strand of DNA (deoxyribonucleic acid) or RNA (ribonucleic acid), or a specific protein of bacteria, viruses, fungi and parasites involved in infectious contamination, among which mention may be made, by way of example, of the family of coronaviruses of SARS (severe acute respiratory syndrome), HIV (human immunodeficiency virus), influenza, Ebola virus, Dengue, Chikungunya or Zika. In addition, other types of analytes may be a hormone, an enzyme, glucose, exogenous chemical compounds (ethanol, pharmaceutical or narcotic compounds and/or their metabolites), coagulation parameters (in particular factors VII, V, X, II and fibrinogen which are present in blood plasma), endogenous proteins (for example the proteins released by the heart muscle), metabolites, nucleic acids, etc., for which it is sought to determine the presence in the biological sample and/or the concentration.

Furthermore, such biological, physiological or physical parameters are, for example, body temperature, blood pressure, heart rate, blood oxygen level, pH, etc.

Conventionally, it is known to take a biological sample and analyze it in the laboratory. Thereafter, a biologist draws up an analysis report, and the subject from whom the sample has been taken is authorized or not authorized to enter the restricted-access area, depending on the content of the report.

However, such a procedure is not entirely satisfactory.

Indeed, such a procedure may be automated with some difficulty, and it takes time, in particular when linked to the logistics associated with the handling of the samples taken, with the result that it cannot be applied, for example, at the entrance to a confined means of transport (aircraft, train, ship, etc.) in order to determine whether or not each person who has booked a plane or train ticket can board, depending on their state of health or their level of contamination. However, such means of transport are particularly sensitive to the effects of the state of health induced by visitors or by employees, in particular because they can either endanger the safety of users or bring about contamination.

In the same way, such a procedure cannot be applied on a large scale, for example for testing potential participants and staff attending a sporting, cultural or religious gathering, or for screening visitors to or staff of a social, medico-social or health establishment, for example a residential establishment for dependent elderly people.

The reasons limiting current use are in particular the minimum time to obtain the test result (generally greater than ten minutes or so), the moderate reliability of the tests (existence of a not insignificant rate of false negatives) and the difficult traceability of the samples, which may give rise to delays, errors or fraud.

An object of the invention is therefore to make available an access device making it possible, in a simple, rapid and automated manner, to generate an access key allowing subjects to be screened according to their state of health.

DISCLOSURE OF THE INVENTION

To this end, the invention relates to an access device of the aforementioned type, comprising a support, a sensor and an access control stage, the support comprising a disposable part and a retainable part, the sensor being carried by the disposable part of the support and being configured to measure at least one health parameter of a subject, and to deliver a detection signal representative of the measurement of each health parameter, the access control stage being carried by the retainable part of the support and being configured to store, preferably in encrypted form, access information depending on the detection signal delivered by the sensor, the retainable part of the support being able to be mechanically separated from the disposable part in order to form an access key which, depending on the access information, permits or prohibits access to the restricted-access area. The retainable part is thus configured to form a functional unit, independent of the disposable part. Following its separation from the disposable part, the retainable part forms a key that can be used independently of the disposable part. Separation is understood to mean a definitive separation or a disconnection making it possible to reconnect the key part to a new disposable sensor part, which will make it possible to reuse the key later.

Indeed, such an access device combines:
- a sensor intended to measure, in an autonomous and on-board manner, each health parameter of the subject, for example to measure the presence of at least one predetermined analyte in a biological sample taken from the subject; and
- an access control stage, intended to store information depending on such detection, and coupled or not coupled to biometric data.

By separating the retainable part (which is provided with the access control stage) from the disposable part (which contains the used biosensor), an access key is obtained that can be used as an access permit.

In this way, the intervention of a biologist is not required, and the subject is able to obtain the access key quickly and automatically. In addition, the disposable part, which is potentially contaminated (or even contaminating), can simply be discarded, for example in a secure container provided at the test site, and/or immersed in a disinfectant solution in order to neutralize any possible danger it may pose.

Depending on the access information stored on the access key, for example read by a reader arranged at an entrance to a restricted-access area, the subject may or may not be authorized to access said area.

It follows that the access device according to the invention has the following advantages:
- ergonomics and hygiene: the test is potentially non-invasive (for example when it is based on the use of the subject's saliva as a biological sample), allowing human subjects to perform it themselves. The potentially soiled sensor is detached and discarded. In addition, the screening of the test subjects can be done without any human intervention, for example by means of automated gantries;
- manufacturing cost: by virtue of its structure, such a device is simple to produce and therefore has a low manufacturing cost;
- speed of the test: the sensor can be optimized to deliver a detection signal after just a few minutes. In addition, in territories where legislation so permits, the test can be carried out without the intervention of a biologist, such that the access key is able to be obtained quickly.

According to other advantageous aspects of the invention, the access device has one or more of the following features, taken in isolation or in any technically possible combination:
- the sensor is intended to be brought into contact with a biological sample taken from a subject, the sensor being further configured to deliver a detection signal representative of the presence or absence of at least one predetermined analyte in the biological sample, the detection signal also being representative of the presence or absence of at least one predetermined analyte in the biological sample;
- the access information comprises the detection signal and/or data relating to the presence or absence of at least one predetermined analyte in a biological sample taken from the subject and/or data relating to a time stamp and to a period of validity of an access authorization and/or data relating to a place of validity of the access authorization and, preferably, a unique identifier of the subject;
- the access control stage is further configured to store a unique identifier of the subject from whom the biological sample has been taken;
- the access control stage is configured to receive the detection signal, the access control stage being further configured to establish, with an external data processing unit, a wireless link, preferably encrypted, and to transmit to the data processing unit, via the wireless link, the detection signal received from the sensor, the access control stage also being configured to receive from the data processing unit, via the wireless link, an analysis signal established on the basis of the detection signal and comprising the access information;
- the access control stage is also configured to receive energy via the wireless link, the access control stage being configured to take at least some of the received energy in order to generate an interrogation signal for the sensor, the sensor being configured to deliver the detection signal following reception of the interrogation signal generated by the access control stage;
- the access control stage is electrically connected to the sensor by means of a connection bus, the retainable part of the support being configured to be separated from the disposable part by being broken along a predetermined fracture line, the connection bus being configured to sever, preferably at the fracture line, upon separation of the retainable part from the disposable part.

By way of example, in this particular embodiment, the retainable part can be made up of several detachable parts, which each contain an access control stage and are arranged one after the other and linked together by the connection bus, so as to receive information from the same sample. It is important to note that once the test has been carried out, the fracture at the connection bus does not affect the information already transmitted to the one or more access control stages; or
- the access control stage is electrically connected to the sensor by means of a connection bus, the retainable part of the support being configured to be separated from the disposable part by being peeled off at a predetermined bonding zone, the electrical continuity of the connection bus in the bonding zone being provided by a conductive adhesive or by vias configured to break during the peeling-off. It is important to note that once the test has been carried out, the unpeeling at the connection bus does not affect the information already transmitted to the access control stage; or the access control stage is electrically connected to the sensor by means of a connection bus, the retainable part of the support being configured to be separated from the disposable part by disconnection, the two parts are connected to each other by a multi-contact connector, for example a USB key system or a memory card. The male part of the connector may be contained either on the retainable part or on the disposable part. In this case, the connection bus is configured to be interrupted preferably at the disconnection zone, during the separation of the retainable part 26 from the disposable part 24, and in this way the retainable PASS part, once reset, is reusable with a new disposable sensor part. It is important to note that once the test has been carried out, the disconnection does not affect the information already transmitted to the access control stage;

the access control stage forms at least part of a radio tag, preferably capable of implementing a near-field communication;

the sensor and the retainable part of the support are spaced apart from each other, a distance between the sensor and the retainable part of the support being greater than a predetermined contamination limit.

In addition, the invention relates to an access key generation system comprising the access device as defined above, and a data processing unit configured to receive the detection signal, to generate, from the received detection signal, an analysis signal comprising the access information, and to provide the analysis signal to the access control stage.

In addition, the invention relates to an access control method for authorizing or not authorizing the access of a subject to a restricted-access area, the method using the access device as defined above and comprising the steps of:

measuring, by means of the sensor, at least one health parameter of the subject;

generating the access information according to the detection signal;

storing the access information in the access control stage; and separating the retainable part of the support from the disposable part in order to form the access key.

According to another advantageous aspect of the invention, the access control method has one or more of the following features, taken in isolation or in any technically possible combinations:

the method additionally comprises recording, in the access control stage, a unique identifier of the subject from whom the biological sample has been taken;

the method additionally comprises the steps of:

transmitting the detection signal, delivered by the sensor, to a data processing unit via a wireless link, preferably encrypted;

using the data processing unit to analyze the detection signal delivered by the sensor, in order to determine a value of each health parameter, and generating the access information according to the analysis of the detection signal; and after the access information has been generated by the data processing unit, transmitting to the access control stage an analysis signal comprising the access information generated, from the data processing unit, via the wireless link;

the method additionally comprises the steps of:

presenting the formed access key to a reader with which an entrance to the restricted-access area is equipped;

reading, by means of the reader, the access information stored in the access control stage of the access key;

authorizing or not authorizing the subject's access to the restricted-access area according to the access information read;

during the authorization or non-authorization of the access to the restricted-access area, the access to the restricted-access area is authorized if the access information indicates the absence of at least one predetermined analyte in a biological sample taken from the subject or if a value of a health parameter falls within a predetermined range or threshold, and otherwise access is prohibited.

BRIEF DESCRIPTION OF THE DRAWINGS

The invention will be better understood from the description which follows, given solely by way of non-limiting example and made with reference to the appended drawings in which.

DETAILED DESCRIPTION

Figure 1:
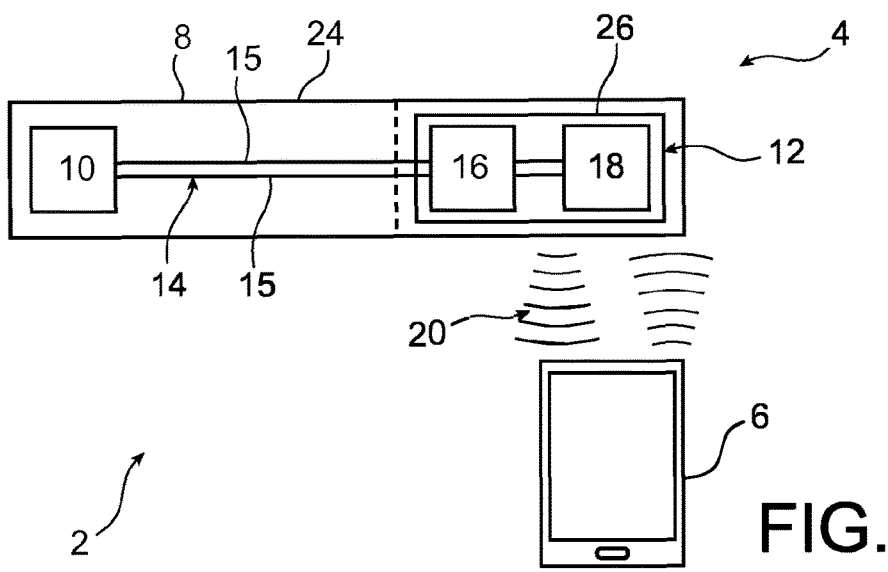
FIG. 1 is a schematic representation of an access key generation system according to the invention.

An access key generation system 2 according to the invention is illustrated in FIG. 1.

A generation system 2 of this kind is, for example, intended for use as a rapid immunological self-test for viral load by electronic bio-detection of a saliva sample.

The generation system 2 is able to provide an access key making it possible to determine whether or not a subject is authorized to access a restricted-access area. As will emerge from the description that follows, such an access key is a physical object, and not a virtual one.

The generation system 2 comprises an access device 4 and a data processing unit 6, which is configured to cooperate with the access device 4 in order to set the parameters of the access key.

Structure

Access Device

As will emerge from the description that follows, the access device 6 is a portable and single-use device.

More precisely, "single-use" within the context of the present invention means that, for a given access device 4, a single subject, or else a single biological sample, is tested, a sensor 10 of the access device preferably being discarded (or even destroyed) after such a test. On the other hand, and as will be described later, the access key itself is able to be presented numerous times during checks intended to determine whether the subject is authorized or not authorized to access one or more restricted-access areas, in a restricted or unrestricted time window.

The access device 4 comprises a support 8, a sensor 10, and an integrated circuit 12 electrically connected to the sensor 10 by means of a connection bus 14.

The sensor 10 is configured to measure at least one health parameter of a subject, each health parameter being representative of a state of health of the subject.

For example, the sensor 10 is configured to measure a temperature or a blood pressure of the subject (with or without contact with the subject), or even a pH of a biological sample obtained from the subject.

According to another example, the sensor 10 is sensitive to at least one predetermined analyte. In this case, the sensor 10 is intended to be brought into contact with a biological sample to be tested, taken from the subject, in order to measure the presence or absence of each predetermined analyte, or even its concentration in the biological sample.

For example, the predetermined analyte is a compound such as a nucleic acid or a protein representative of a microbiological contaminant, such as a viral or bacterial contaminant, and/or an antibody specific to a given antigen, and/or an analyte representative of an altered state of health and/or of an intoxication and/or of a concentration or of a value of a physicochemical parameter.

Furthermore, the sensor 10 is configured to deliver a detection signal representative of the measurement of each predetermined health parameter. For example, the sensor 10 is configured such that, for each predetermined analyte, the detection signal is representative of the presence and/or concentration of the analyte in the biological sample.

By way of example, the biological sample is a bodily fluid, such as breath, saliva, sputum, sebum, sweat, blood or exudate from a wound. For example, the biological sample is obtained from a sample taken from the nasopharyngeal tract or from the oral cavity of the subject (saliva, sputum, etc.).

For example, in the case where the sensor 10 is sensitive to at least one predetermined analyte, said sensor 10 comprises a sensitive surface having a graphene sheet deposited on a rigid substrate (silicone, for example) or on a flexible substrate (polymer). Graphene is a particularly advantageous material for the invention by virtue of its mass production, allowing development of a precise sensor for single use at a reduced cost, and its use in the field of surface chemistry. In this case, the graphene sheet is covered with a thin layer having functional groups (for example a DNA strand, an oligonucleotide, an aptamer, a peptide, an enzyme or an antibody) specific to a given analyte. If the biological sample comprises the analyte, a biological recognition reaction between the functional group and said analyte occurs, leading to immobilization of the analyte, which results in a variation in the electrostatic charge induced at the surface of the graphene sheet. In particular, such a variation in electrostatic charge is all the greater the greater the concentration of analyte in the biological sample. This variation in electrostatic charge leads to a change in the electrical conductance of the graphene sheet, the amplitude of which reflects the concentration of analyte. Such a change in conductance is able to be determined from the detection signal delivered by the sensor 10.

The integrated circuit 12 is configured to receive the detection signal delivered by the sensor 10 and conveyed by the connection bus 14, the latter being produced, for example, by means of electrically conductive tracks 15.

The integrated circuit 12 is also configured to exchange, by wireless communication, signals with the data processing unit 6 for generation of the access key.

Advantageously, the wireless communication module 12 is also configured to receive, wirelessly, energy from the data processing unit 6. Such energy transmission is effected by induction, for example.

The implementation of such wireless energy transmission is advantageous, insofar as it is no longer necessary to use electrical energy storage means at the level of the access device 4.

By way of example, the integrated circuit 12 is configured to take up energy from a wireless link 20 described later.

The integrated circuit 12 comprises a digitization stage 16 and an access control stage 18 electrically connected to each other.

The digitization stage 16 is connected to the sensor 10 in order to receive the analog detection signal delivered by the sensor 10, and to convert it into a digital detection signal applied to the input of the access control stage 18.

As a variant, the digitization stage 16 is not integrated into the integrated circuit 12 but is implemented by means of an independent electronic component. According to another variant, the digitization function is performed by the access control stage 18 itself.

The access control stage 18 is configured to generate an interrogation signal for the sensor 10. In this case, the sensor 10 is configured to deliver the detection signal following receipt of the interrogation signal delivered by the access control stage 18. In particular, the access control stage 18 is configured to generate the interrogation signal from at least some of the energy received by the integrated circuit 12 from the data processing unit 6.

In addition, the access control stage 18 is configured to establish, with the data processing unit 6, a wireless link 20, preferably encrypted. In addition, the access control stage 18 is configured to transmit, to the data processing unit 6 via the wireless link 20, the detection signal that is received from the sensor 10.

Such a wireless link 20 is established in particular by means of an antenna (not shown) of the access control stage 18.

The encryption of the wireless link 20 is advantageous, insofar as such a link transmits a detection signal from which it is possible to extract sensitive data, for example confidential data, relating to the subject from which the biological sample has been taken.

Preferably, the access control stage 18 is also configured to transmit, to the data processing unit 6, via the wireless link 20, information relating to the sensor 10. Such information relating to the sensor 10 is, for example, registered in the access control stage 18 during the manufacture of the access device 4 and is able to be used by the data processing unit 6 during the analysis of the detection signal, as will be described later.

The access control stage 18 is also configured to receive, from the data processing unit via the wireless link 20, an analysis signal established from the detection signal and comprising the access information.

Advantageously, the access control stage 18 is additionally configured to store a unique identifier of the subject whose health parameter(s) is (are) measured. For example, the unique identifier is transmitted to the access control stage 18 by the data processing unit 6, via the wireless link 20.

Advantageously, the access control stage 18 forms at least part of a radio tag, also called an RFID (Radio Frequency IDentification) tag. In this case, the radio tag is preferably able to implement near-field communication (NFC). As a variant, the radio tag is able to implement a wireless communication having a carrier frequency belonging to the ultra-high frequency domain, in particular between 860 MHz (megahertz) and 960 MHz, for example a wireless communication such as defined by the standards EPCglobal or ISO 18000-6C.

The use of RFID technology is particularly advantageous, in particular from the point of view of manufacturing costs. Indeed, such a characteristic confers great simplicity of manufacture on the access device 4 (in particular the wireless communication module 12). As a result, the access device 4 according to the invention is able to be manufactured by mass production and at very low cost, as radio tags are generally very inexpensive.

In addition, the use of RFID technology also enables encryption of the stored data and of the signals exchanged over the air. In this way, there is the potential for the result(s) of the biological sample test to be unalterable and confidential.

The support 8 preferably has an elongate shape. For example, the support 8 is in the form of a strip, a stick, a swab, a tab, etc.

The support 8 comprises a disposable part 24 and a retainable part 26 mechanically connected to each other.

More precisely, and as shown in FIG. 1, the disposable part 24 is equipped with the sensor 10. In addition, the retainable part 26 is equipped with the access control stage 18. Furthermore, the digitization stage 16, when it is not included in the integrated circuit 12, is carried either by the disposable part 24 or by the retainable part 26 of the support 8.

The retainable part 26 of the support 8 is able to be mechanically separated from the disposable part 24 in order to form an access key which, depending on the access information, permits or prohibits access to the restricted-access area.

Of course, the access key itself is not for single use and instead is able to be presented at a plurality of checks, each one intended to authorize or not authorize access, by the subject associated with said key, to the same restricted-access area or to different restricted-access areas.

More precisely, the retainable part 26 of the support 8 is configured to be mechanically separated from the disposable part 24 by breaking, cutting, tearing or unpeeling. In addition, the connection bus 14 is configured to sever during such separation, in particular in such a way as to allow easy separation of the disposable part 24 and the retainable part 26.

Figure 2:
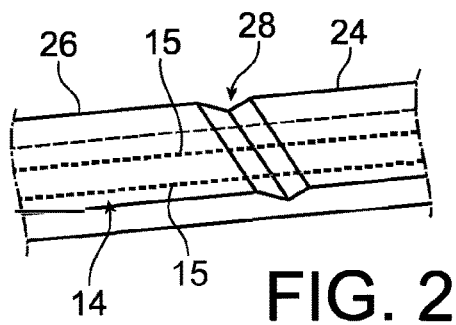
FIG. 2 is a schematic perspective view of a fracture line of a support of a first embodiment of an access device of the access key generation system of FIG. 1.

According to an example illustrated by FIG. 2, the retainable part 26 of the support 8 is configured to be separated from the disposable part 24 by breaking, more precisely by breaking along a predetermined fracture line 28. In this case, the connection bus 14 is configured to sever in particular at the level of the fracture line(s) 28.

In this case, the support 8 is, for example, a component made of molded polymer plastic, the structure of which has a notch defining the fracture line 28 in order to allow it to be broken during mechanical twisting applied to the support 8. The tracks 15 are, for example, made of an easily breakable conductive material, for example a conductive polymer incorporating silver particles in a plastic channel embedded in the support 8. In this way, the access key is able to be used like an access badge or a pre-cut credit card.

Figure 3:
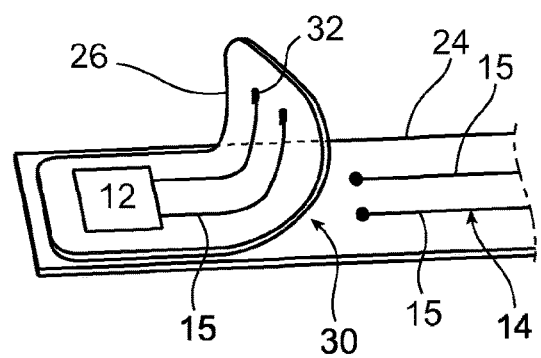
FIG. 3 is a schematic perspective view of a peel-off zone of a support of a second embodiment of an access device of the access key generation system of FIG. 1.

According to another example, illustrated by FIG. 3, the retainable part 26 of the support 8 is configured to be separated from the disposable part 24 by being peeled off at a predetermined bonding zone 30. In this case, when the disposable part 24 and the retainable part 26 of the support 8 are not mechanically separated, the electrical continuity of the connection bus 14 at the level of the bonding zone 30 is provided by a conductive adhesive (for example a conductive adhesive charged with silver microparticles) and/or vias 32. Such vias 32 are configured to break during the unpeeling of the retainable part 26. In the same way, the conductive adhesive is configured so as to no longer provide the electrical continuity of the connection bus 14 after the retainable part 26 has been peeled off.

In this case, the retainable part 26 is, for example, a paper or polymer support comprising the antenna of the access control stage in the form of a flexible printed structure made of conductive ink or of a thin etched metallic layer, commonly referred to as an RFID inlay. Advantageously, to promote the unpeeling of the retainable part 26, the disposable part 24 is provided, at the bonding zone 30, with a suitable non-stick layer.

Advantageously, the access key has an adhesive surface. In this way, the access key is able to be used in the manner of a sticker and, for example, can be stuck onto an identity document, a boarding pass, etc.

Figure 4:
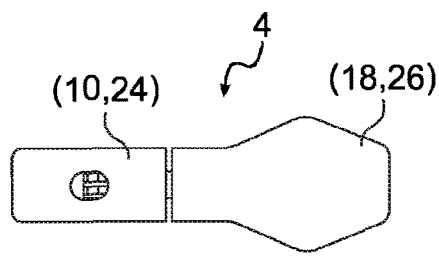
FIG. 4 shows the retainable part of the support, which part is configured to be separated from the disposable part by disconnection.
Figure 4:
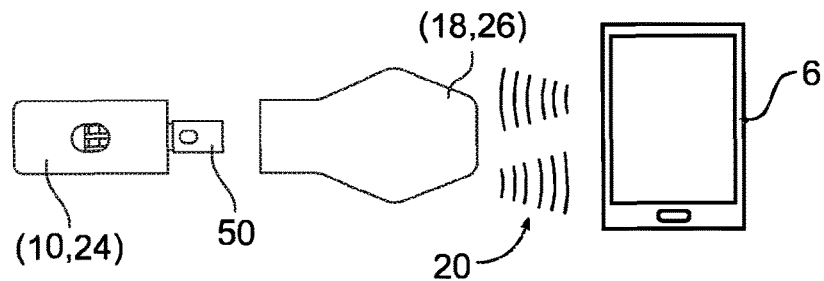

According to an example illustrated in FIG. 4, the retainable part 26 of the support 8 is configured to be separated from the disposable part 24 by disconnection, more precisely the two parts are connected to each other by a multi-contact connector 50, by way of example a USB key system or a memory card. The male part of the connector can be contained either on the retainable part 26 or on the disposable part 24. In this case, the connection bus is configured to be interrupted preferably at the level of the disconnection zone, during the separation of the retainable part 26 from the disposable part 24. The retainable part 26, thus disconnected from the disposable part 24, can then be used to cooperate with the processing unit 6.

According to all the exemplary embodiments, the retainable part 26 is configured to exercise the key function independently of the disposable part. The functional elements mentioned above (for example integrated circuit, energy storage, information storage) are thus distributed between the disposable part and the retainable part in such a way as to allow the retainable part to exercise its key function independently.

Preferably, the access device 4 is such that, before the separation of the disposable part 24 from the retainable part 26 of the support 8, the sensor 10 and the retainable part 26 of the support 8 are spaced apart from each other, the distance between the sensor 10 and the retainable part 26 of the support 8 being greater than a predetermined contamination limit. This is advantageous insofar as contamination of the retainable part 26, during the use of the access device 4 to test the biological sample, is thus potentially avoided.

Data Processing Unit

As indicated above, the data processing unit 6, shown in FIG. 1, is configured to receive the detection signal from the access control stage 18 via the wireless link 20, and to analyze said detection signal. In particular, the data processing unit 6 is able to analyze the detection signal, preferably in correspondence with the sensor 10 from which said detection signal originates, in order to determine the health parameters, for example in order to determine the presence and/or the concentration of each corresponding predetermined analyte in the biological sample.

For example, the data processing unit 6 is a smartphone running a dedicated application for processing detection signals delivered by predetermined sensors 10.

The data processing unit 6 is also configured to generate, from such an analysis of the received detection signal, corresponding access information.

Preferably, the access information comprises data relating to the presence or absence of each predetermined analyte in the biological sample, or even to its concentration in the biological sample, or else relating to the value of predetermined physical, physiological or biological parameters.

More preferably, the access information comprises data relating to a time stamp and to a period of validity of an access authorization and/or data relating to a place of validity of the access authorization. This is advantageous insofar as the validity of the results of the test of the subject and/or of the biological sample taken from said subject, carried out by means of the generation system 2, is thus limited to a given spatio-temporal window. Such a spatio-temporal window is, for example, associated with a given event, such as, without limitation, a phase of boarding a given commercial flight. Of course, such a spatio-temporal window is able to be associated with any event requiring monitoring of subjects in order to afford them the possibility of accessing a restricted-access area.

Furthermore, the data processing unit 6 is configured to transmit an analysis signal to the access control stage 18, via the wireless link 20, the analysis signal comprising the access information generated. As a result, the analysis signal depends on the detection signal delivered by the sensor 10.

Advantageously, the access information also comprises the unique identifier of the subject whose health parameters have been measured (for example using a biological sample taken from said subject). Such a feature is advantageous insofar as it reinforces the traceability of the access key and reduces the risks of fraud.

For example, in this latter case, the data processing unit 6 is configured to offer the possibility for the subject to identify himself by means of a secure portal. Of course, any other means of identifying the subject unambiguously is conceivable.

Functioning

The functioning of the generation system 2 will now be described.

To determine whether or not a subject is authorized to access a restricted-access area, each predetermined health parameter of the subject is measured by means of the sensor 10 of the access device 4 of this generation system 2. For example, a biological sample is taken from said subject, then the sensor 10 is brought into contact with the biological sample that has been taken.

The sensor 10 then delivers the corresponding detection signal, which is digitized by the digitization stage 16 and applied to the input of the access control stage 18. The detection signal delivered by the sensor 10 is then analyzed to determine each health parameter, for example to determine the presence or absence of at least one analyte in the biological sample, and to generate access information depending on a result of said analysis of the detection signal.

In particular, a wireless link 20, preferably encrypted, is established between the access control stage 18 and the data processing unit 6. In this case, the detection signal received by the access control stage 18 and coming from the sensor 10 is transmitted to the data processing unit 6 via the wireless link 20, such that the analysis of the detection signal and the generation of the access information are implemented by the data processing unit 6.

The access information is then stored in the access control stage 18. Preferably, the access information is stored in the access control stage 18 in encrypted form. In this way, the access information stored in the access control stage 18 can only be read by readers that are configured specifically to decrypt it. This increases the security of the access key and reduces the chances of the information it contains being rewritten by a malicious third party.

In particular, to allow such storage of access information, the data processing unit 6 sends to the access control stage 18, via the wireless link 20, an analysis signal comprising the access information.

Finally, the retainable part 26 of the support 4 is separated from the disposable part 24 to form the access key.

Preferably, the analysis signal further comprises a unique identifier of the subject from which the biological sample has been taken. In this case, the data processing unit 6 also transmits the unique identifier for its storage in the access control stage.

Once the access key has been detached from the disposable part 24 of the support 8, the access key is presented to a reader with which an entrance to the restricted-access area is equipped.

The reader then reads the access information stored in the access control stage 18 of the access key, after which, depending on the access information that is read, the subject is authorized or not authorized to access the restricted-access area.

For example, access to the restricted-access area is authorized if the access information indicates the absence of at least one analyte in the biological sample, or if a value of a health parameter belongs falls within a predetermined range or threshold, and access is otherwise prohibited.

Furthermore, the disposable part 24 of the support 8, having been separated from the retainable part 26 of the support 8, is preferably forwarded to a biological waste treatment stream and/or immersed in a disinfectant solution in order to neutralize its possible dangerousness.

As a variant, the data processing unit is integrated in the reader intended to authorize or not authorize access of the subject to the restricted-access area, the reader then carrying out the analysis of the detection signal.

In this case, the detection signal stored in the access control stage 18 forms at least part of the access information. In such a variant, the wireless link is directly established with the reader for the transmission of the detection signal.

In addition, in this case, the access device 4 is preferably equipped with an energy storage member intended to supply the access control stage with the energy necessary for its operation.

Such an energy storage member is, for example, charged at the time of manufacture of the access device 4. According to another example, the energy storage member is charged by means of a wireless link, said wireless link being established, for example, to transmit the unique identifier of the subject to the access control stage 18, before the health parameters of said subject are measured by the sensor 10.

According to another variant, the access key generation system 2 does not have a data processing unit, the access control stage 18 being configured to analyze the detection signal in order to establish the access information.

In this case also, an energy storage member is advantageously provided in the access device 4 in order to supply the access control stage 18 with the energy necessary for its operation.

The invention claimed is:

1. A portable access device for accessing a restricted-access area, comprising a support, a sensor and an access control stage, wherein
the portable access device is for single use in that the sensor is capable of being brought into contact with a biological sample taken from a subject,
the support comprises a disposable part and a retainable part, the sensor is capable of being carried by the disposable part of the support and is configured to measure at least one health parameter of a subject, and to deliver a detection signal representative of the measurement of each health parameter, the access control stage is capable of being carried by the retainable part of the support and is configured to store access information depending on the detection signal delivered by the sensor, and the retainable part of the support is capable of being mechanically separated from the disposable part in order to form an access key which, depending on the access information, permits or prohibits access to the restricted-access area, wherein the access control stage is electrically connected to the sensor by means of a connection bus, the retainable part of the support being configured to be separated from the disposable part by being broken along a predetermined fracture line, the connection bus being configured to sever upon separation of the retainable part from the disposable part.

2. The access device of claim 1, wherein the sensor is configured to deliver a detection signal representative of the presence or absence of at least one predetermined analyte in the biological sample, the detection signal also being representative of the presence or absence of at least one predetermined analyte in the biological sample.

3. The access device of claim 1, wherein the sensor is composed of a graphene sheet, said graphene sheet being covered with a thin layer having functional groups specific to a given analyte.

4. The access device of claim 1, wherein the access information comprises the detection signal and/or data relating to the presence or absence of at least one predetermined analyte in a biological sample taken from the subject and/or data relating to a time stamp and to a period of validity of an access authorization and/or data relating to a place of validity of the access authorization.

5. The access device of claim 4, wherein the access information further comprises a unique identifier of the subject.

6. The access device of claim 1, wherein the access control stage is further configured to store a unique identifier of the subject.

7. The access device of claim 1, wherein the access control stage is configured to receive the detection signal,
wherein the access control stage being further configured to establish, with an external data processing unit, and a wireless link, and to transmit, to the data processing unit via the wireless link, the detection signal received from the sensor, and the access control stage also being configured to receive, from the data processing unit via the wireless link, an analysis signal established on the basis of the detection signal and comprising the access information.

8. The access device of claim 7, wherein the access control stage is also configured to receive energy via the wireless link, the access control stage being configured to take at least some of the received energy in order to generate an interrogation signal for the sensor, the sensor being configured to deliver the detection signal following reception of the interrogation signal generated by the access control stage.

9. The access device of claim 1, wherein the access control stage is electrically connected to the sensor by means of a connection bus, the retainable part of the support is connected to the disposable part by a multi-contact connector, and the retainable part is configured to be separated from the disposable part by disconnection, the connection bus being configured to be interrupted, upon separation of the retainable part from the disposable part, a male part of the connector being able to be contained either on the retainable part or on the disposable part.

10. The access device of claim 1, wherein the access control stage forms at least part of a radio tag.

11. The access device of claim 10, wherein the access control stage is able to implement a near-field communication.

12. An access key generation system comprising the access device of claim 1, and a data processing unit configured to receive the detection signal, to generate, from the received detection signal, an analysis signal comprising the access information, and to provide the analysis signal to the access control stage.

13. A portable access device for accessing a restricted-access area, comprising a support, a sensor and an access control stage, wherein
the portable access device is for single use in that the sensor is capable of being brought into contact with a biological sample taken from a subject, the support comprises a disposable part and a retainable part, the sensor is capable of being carried by the disposable part of the support and is configured to measure at least one health parameter of a subject, and to deliver a detection signal representative of the measurement of each health parameter, the access control stage is capable of being carried by the retainable part of the support and is configured to store access information depending on the detection signal delivered by the sensor, and the retainable part of the support is capable of being mechanically separated from the disposable part in order to form an access key which, depending on the access information, permits or prohibits access to the restricted-access area, wherein the access control stage is electrically connected to the sensor by means of a connection bus, the retainable part of the support being configured to be separated from the disposable part by being peeled off at a predetermined bonding zone, the electrical continuity of the connection bus in the bonding zone being provided by a conductive adhesive or by vias configured to break during the peeling-off.

14. A portable access device for accessing a restricted-access area, comprising a support, a sensor and an access control stage, wherein
the portable access device is for single use in that the sensor is capable of being brought into contact with a biological sample taken from a subject, the support comprises a disposable part and a retainable part, the sensor is capable of being carried by the disposable part of the support and is configured to measure at least one health parameter of a subject, and to deliver a detection signal representative of the measurement of each health parameter, the access control stage is capable of being carried by the retainable part of the support and is configured to store access information depending on the detection signal delivered by the sensor, and the retainable part of the support is capable of being mechanically separated from the disposable part in order to form an access key which, depending on the access information, permits or prohibits access to the restricted-access area, wherein the sensor and the retainable part of the support are spaced apart from each other, a distance between the sensor and the retainable part of the support being greater than a predetermined contamination limit.

15. An access control method for authorizing or not authorizing the access of a subject to a restricted-access area, the method using a portable access device for accessing a restricted-access area, comprising a support, a sensor and an access control stage, wherein the portable access device is for single use in that the sensor is capable of being brought into contact with a biological sample taken from a subject, the support comprises a disposable part and a retainable part, the sensor is capable of being carried by the disposable part of the support and is configured to measure at least one health parameter of a subject, and to deliver a detection signal representative of the measurement of each health parameter, the access control stage is capable of being carried by the retainable part of the support and is configured to store access information depending on the detection signal delivered by the sensor, and the retainable part of the support is capable of being mechanically separated from the disposable part in order to form an access key which, depending on the access information, permits or prohibits access to the restricted-access area, and comprising the steps of:

measuring, by means of the sensor, at least one health parameter of the subject;

generating the access information according to the detection signal;

storing the access information in the access control stage; and separating the retainable part of the support from the disposable part in order to form the access key, in the access control stage, a unique identifier of the subject.

16. The access control method of claim 15, further comprising:

transmitting the detection signal, delivered by the sensor, to a data processing unit via a wireless link;

using the data processing unit to analyze the detection signal delivered by the sensor, in order to determine a value of each health parameter, and generating the access information according to the analysis of the detection signal; and after the access information has been generated by the data processing unit, transmitting to the access control stage an analysis signal comprising the access information generated, from the data processing unit, via the wireless link.

17. The access control method of claim 16, wherein the detection signal, delivered by the sensor, to a data processing unit via a wireless link, is encrypted.

18. The access control method of claim 15, further comprising the steps of:

presenting the formed access key to a reader with which an entrance to the restricted-access area is equipped;

reading, by means of the reader, the access information stored in the access control stage of the access key; and authorizing or not authorizing the subject's access to the restricted-access area according to the access information read.

19. The access control method of claim 18, wherein, during the authorization or non-authorization of the access to the restricted-access area, the access to the restricted-access area is authorized if the access information indicates the absence of at least one predetermined analyte in a biological sample taken from the subject or if a value of a health parameter falls within a predetermined range, and otherwise access is prohibited.

* * * * *